(12) United States Patent
Shimizu et al.

(10) Patent No.: US 6,664,540 B2
(45) Date of Patent: Dec. 16, 2003

(54) MICROPROBE AND SAMPLE SURFACE MEASURING APPARATUS (75) Inventors: Nobuhiro Shimizu, Chiba (JP); Yoshiharu Shirakawabe, Chiba (JP); Hiroshi Takahashi, Chiba (JP); Chiaki Yasumuro, Chiba (JP)

(73) Assignee: Seiko Instruments Inc., Chiba (JP)

( * ) Notice: Subject to any disclaimer, the term of this patent is extended or adjusted under 35 U.S.C. 154(b) by 200 days.

(21) Appl. No.: 09/778,459

(22) Filed: Feb. 7, 2001

(65) Prior Publication Data

US 2001/0028033 A1 Oct. 11, 2001

(51) Int. Cl.[7] ............................................. G01N 23/00
(52) U.S. Cl. .......................................... 250/309; 73/105
(58) Field of Search ................................ 250/309, 306; 73/105

(56) References Cited

U.S. PATENT DOCUMENTS 6,079,255 A * 6/2000 Binnig et al. .................. 73/105

* cited by examiner

*Primary Examiner*—John R. Lee
*Assistant Examiner*—Phillip A. Johnston
(74) *Attorney, Agent, or Firm*—Adams & Wilks

(57) ABSTRACT

A microprobe has a cantilever having a first lever portion having a free end portion, a second lever portion having a front end portion from which the first lever portion projects, and a support portion for supporting the second lever portion. A piezoresistive element is disposed on the second lever portion for bending the second lever portion.

20 Claims, 7 Drawing Sheets

MICROPROBE AND SAMPLE SURFACE MEASURING APPARATUS

BACKGROUND OF THE INVENTION

1. Field of the Invention

The present invention relates to a microprobe constituted by a cantilever provided with a piezoresistive element on a surface of a semiconductor substrate and a sample surface measuring apparatus observing a very small area (nanometer order) of the sample surface by using the microprobe.

2. Description of the Prior Art

Currently, as a microscope for observing a very small area of nanometer order on a surface of a sample, there is known a Scanning Probe Microscope (SPM). In the field of SPM, an Atomic Force Microscope (AFM) uses a microprobe constituted by a cantilever provided with a stylus at a front end portion thereof and the stylus of the cantilever is made to scan along a surface of a sample constituting an observation object and atomic force (attractive force or repulsive force) caused between the surface of the sample and the stylus is detected as an amount of bending the cantilever to thereby measure the shape of the surface of the sample.

It is known that the above-described microprobe is classified into a microprobe of an optical lever type and a microprobe of a self detection type by a difference in a system of detecting the bending amount of the cantilever. The optical lever type microprobe referes to a microprobe used in a system in which a laser beam is irradiated to an end portion of the cantilever constituting the microprobe and the above-described bending amount is detected by measuring a change in an angle of reflection thereof. This system is also known as an optical lever detection system.

The optical lever type microprobe has the advantage that it is capable of being fabricated inexpensively in comparison with the self detection type microprobe. On the other hand, the optical lever type microprobe has the drawback that when it is used in an atomic force microscope, it is necessary to finely adjust an irradiation angle of a laser beam irradiated to the cantilever and a position of a photodiode for detecting a reflection beam from the cantilever and the like. In particular, which interchanging the cantilever which is frequently carried out, the fine adjustment must be carried out repeatedly, which is troublesome.

Meanwhile, the self detection type microprobe refers to a microprobe forming a piezoresistive element on the cantilever and capable of detecting the bending amount of the cantilever by measuring a variation in a resistance value thereof.

According to the self detection type microprobe, when used in an atomic force microscope, since a detector (piezoresistive element) for detecting the bending amount of the cantilever is formed at the microprobe per se, there is provided an advantage in which in interchanging the cantilever, the troublesome operation of adjusting the position of the detector is not necessary and the observation of a sample can be started swiftly. On the other hand, in comparison with the optical lever type microprobe, there is provided a drawback in which the constitution of the microprobe becomes complicated and the microprobe becomes difficult to provide inexpensively to a user.

Figure 10:
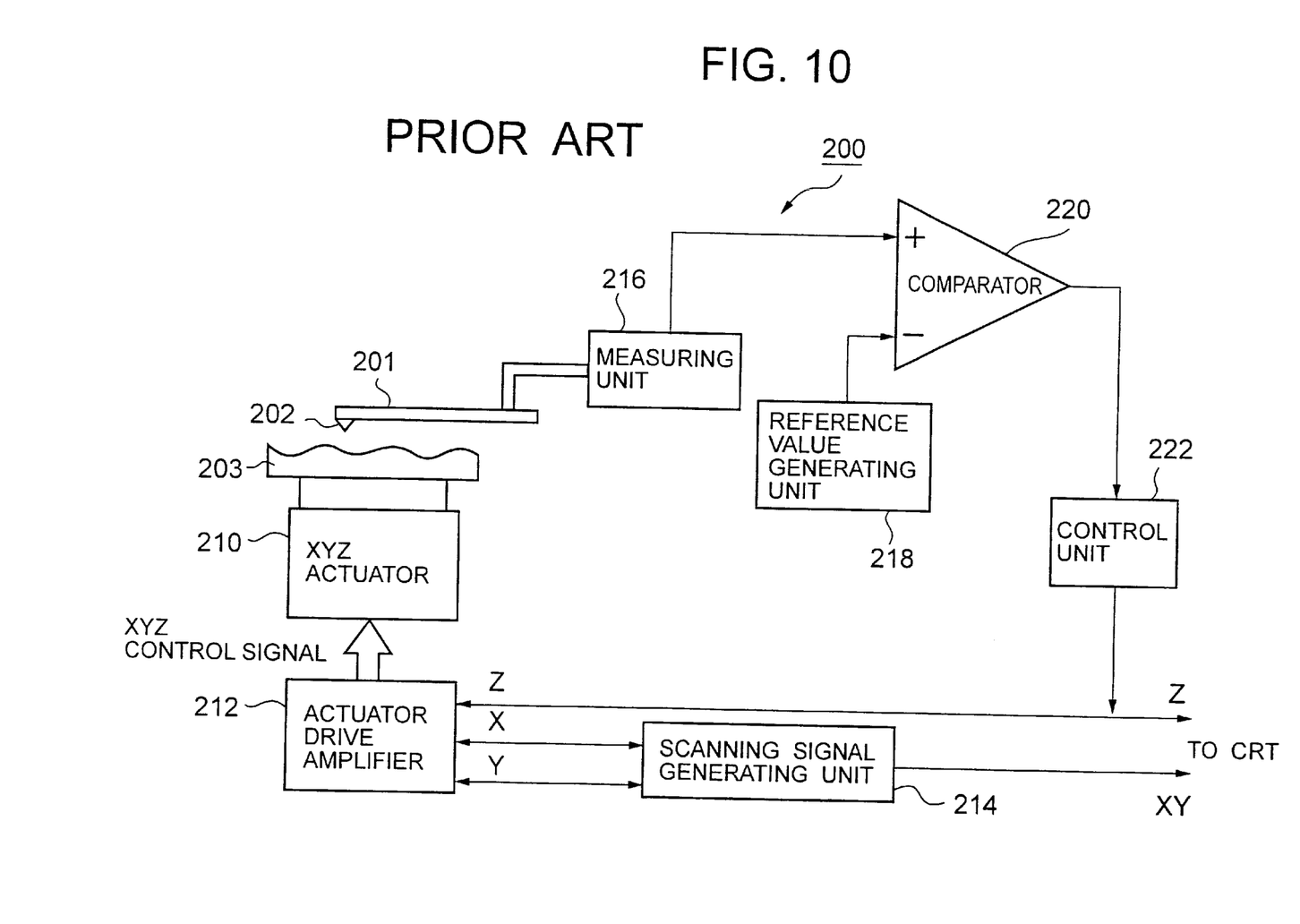
FIG. 10 is a block diagram showing an outline constitution of an atomic force microscope using a conventional self detection type microprobe.

FIG. 10 is a block diagram showing an outline constitution of an atomic force microscope using particularly the above-described self detection type microprobe in these microprobes. In FIG. 10, an atomic force microscope 200 comprises a microprobe 201 (corresponding to the above-described self detection type microprobe) provided with a sharpened stylus 202 directed toward a surface of a sample 203 at its front end portion, an XYZ actuator 210 for finely moving the sample relative to the microprobe 201 in the horizontal direction (X, Y direction) and the vertical direction (Z direction), an actuator drive amplifier 212 for generating an XYZ control signal for driving the XYZ actuator 210, a scanning signal generating unit for generating a signal (scanning signal) for finely moving the sample 203 at constant speed in a predetermined range in the above-described X and Y directions, a measuring unit 216 for acquiring a detection signal provided from a bending detecting portion (the above-described detector: piezoresistive element) on the microprobe 201, a reference value generating unit 128 for generating a detection value in a steady state of the above-described bending detecting portion, that is, a reference value for detecting irregularities of the surface of the sample 203, a comparator 220 for deriving an actual bending amount of the microprobe 201 by comparing signals respectively provided from the measuring unit 216 and the reference value generating unit 218 and a control unit 222 for generating a signal in correspondence with a displacement of the XYZ actuator 210 in Z direction based on a signal provided from the comparator 220.

A brief explanation will be given of operation of the atomic force microscope 200 as follows. First, the user fixes the sample 203 constituting the observation object onto a stage on the XYZ actuator 210 and attaches the microprobe 201 at a comparatively remote position above thereof. Normally, the microprobe 201 is arranged with an electrode terminal for taking out a signal from the above-described bending detecting portion at an end portion thereof disposed opposedly to the stylus 202 and on a face opposed thereto in the longitudinal direction, normally, the microprobe 201 is provided separately from the atomic force microscope as an attachable and detachable cartridge type one facilitating electric connection between the electrode terminal and the measuring unit 216 and fixing an end portion thereof on the side of the electrode terminal.

After preparation before observing the sample has been finished in this way, successively, it is necessary to make the microprobe 201 sufficiently proximate to the sample 203 to a degree that the stylus 202 produces atomic force between the stylus 202 and the surface of the sample 203. The proximity control is carried out firstly, while making the sample 203 being proximate to the stylus 202 by a Z-axis rough movement mechanism (not illustrated) in the XYZ actuator 210, by monitoring whether a predetermined amount of signal can be acquired from the above-described bending detecting portion by the measuring unit 216.

The Z-axis rough movement mechanism in the XYZ actuator 210 is instructed by a computer (not illustrated) for controlling operation of the atomic force microscope 200 under a predetermined condition via the user and is operated based on a Z control signal generated via the actuator drive amplifier 212.

Further, the above-described predetermined amount of signal acquired in the measuring unit 216 is a signal indicating detection of the atomic force between the stylus 202 and the surface of the sample 203 and is actually informed by a signal outputted from the comparator 220. In this case, the resistance value of the piezoresistive element per se constituting the bending detecting portion is varied by conditions other than bending such as temperature condition or the like and accordingly, the reference value of the reference value generating unit 218 constituting one of comparison objects of the comparator 220, provides a reference resistance value for removing the unnecessary variation information from a variation in the resistance value measured at the bending detecting portion.

After finishing the above-described proximity control, at the scanning signal generating unit 214, there is generated a scanning signal for instructing a movement in a predetermined range set on the computer, mentioned above, that is, in a plane range (XY range) in the XYZ actuator. Normally, the scanning signal is a signal for realizing so-to-speak raster scanning in which after finishing scanning operation in X direction while fixing a Y-axis point, the scanning is moved to a successive Y-axis point and the scanning operation in X direction is carried again.

The scanning signal is inputted to the actuator drive amplifier 212, amplified pertinently to current or voltage sufficient for driving the XYZ actuator 210 and thereafter inputted to the XYZ actuator 210 as an XY control signal. The XYZ actuator 210 actually moves the sample 203 on the stage in X and Y directions by inputting the XY control signal.

While repeating the movement of the sample 203 on the XY plane by the above-described XYZ actuator 210, the measuring unit 216 always acquires a signal from the bending detecting portion of the microprobe 201 and a signal in correspondence with the bending amount of the microprobe 201 is outputted from the comparator 220.

In this case, as measurement modes of the atomic force microscope 200, actually, there are various measurement modes of a height constant mode for maintaining constant a height between the stylus 202 and the sample 203 after the proximity control and regarding the bending amount of the microprobe 201 as an irregularity signal of the sample 203, and a bending constant mode for controlling a Z-axis fine movement mechanism (not illustrated) of the XYZ actuator 210 by a feedback control such that the bending amount of the microprobe 201 becomes constant and regarding a control signal required for the feedback control as the irregularity signal of the sample 203 and so on, however, it is assumed here that the bending constant mode is selected.

Therefore, the sample 203 is moved in a constant range on the XY plane and is finely moved in the Z-axis direction by feedback control of the Z-axis fine movement mechanism in the bending constant mode. Simultaneously therewith, the XY control signal and the Z control signal in accordance with operation of the above-described XYZ actuator 210 are inputted to a display apparatus (CRT) and a user can be informed of the surface information of the sample 203.

However, as mentioned above, the atomic force microscope 200 needs the XYZ actuator provided with the fine movement mechanism in the Z-axis direction in addition to the fine movement mechanism in X and Y directions for carrying out the fine movement control in the Z-axis direction, which constitutes a factor hampering downsized formation of the apparatus constituting the microscope. Further, the XYZ actuator is generally formed by piezoelectric elements and is not necessarily regarded to be provided with sufficient response speed, further, considerable power is needed for driving thereof and accordingly, even in the fine movement in the Z-axis direction, the fine movement constitutes a factor of hampering a reduction in power consumption.

Figure 11:
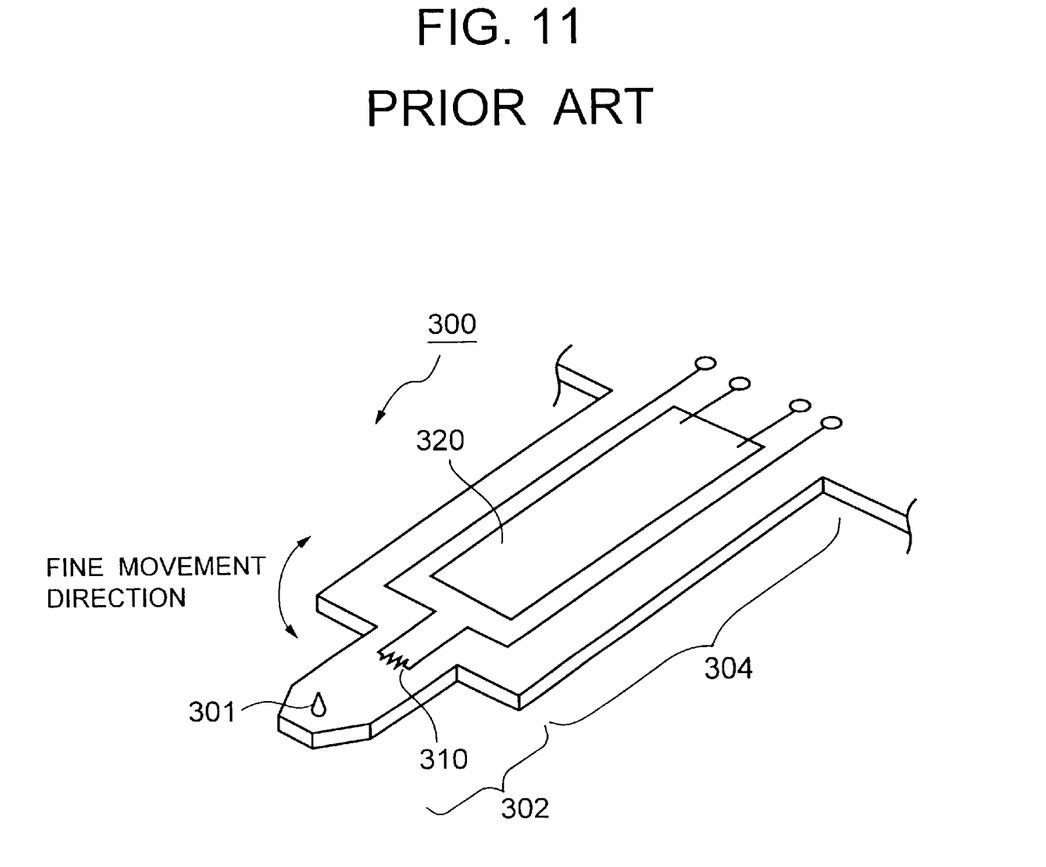
FIG. 11 is a view showing a conventional microprobe having Z-axis fine movement function.

Hence, in constituting the apparatus, there is known a microprobe provided with a Z-axis fine movement function on a cantilever in order to exclude the Z-axis fine movement mechanism by the actuator. FIG. 11 is a view showing a microprobe having the Z-axis fine movement function. In FIG. 11, a microprobe 300 is formed with the stylus 201 and a bending detecting portion 310 (piezoresistive element) at a first lever portion 302 enabling flexible bending by a free end and is formed with an actuator portion 320 on a second lever portion 304.

The actuator portion 320 comprises a piezoelectric element of ZnO or the like, is capable of elongating and contracting in the longitudinal direction of the second lever portion 304 by applying current, as a result, the second lever portion 304 is bent in a direction orthogonal to the plane by the elongating and contracting operation. That is, the fine movement of the microprobe 300 in the Z-axis direction is realized by the actuator portion 320 on the probe.

However, according to the microprobe having the Z-axis fine movement function as shown by FIG. 11, there are adopted piezoelectric elements similar to those in the conventional XYZ actuator as the actuator for realizing the Z-axis fine movement function and accordingly, power consumption cannot be reduced.

Further, the microprobe is very small and accordingly, by providing, on a silicon substrate constituting a base member thereof, in addition to the piezoresistive elements constituting the bending detecting portion, the piezoelectric members having a material quite different from the material of the piezoresistive element, there poses a problem in which not only steps of fabricating thereof become complicated but also a thickness of the cantilever portion is increased and it is difficult to ensure sufficient response speed.

The invention has been carried out in view of the drawback of the conventional technology and it is an object thereof to provide a microprobe enabling to finely move a cantilever by forming a piezoresistive element on the cantilever and a sample surface measuring apparatus using the microprobe.

SUMMARY OF THE INVENTION

A microprobe is constituted by a first lever portion having a free end formed with a stylus, a second lever portion projected with a first lever portion at a front end portion thereof and a support portion for supporting the second lever portion and a piezoresistive element for bending the second lever portion is provided on the second lever portion.

DETAILED DESCRIPTION OF THE PREFERRED EMBODIMENTS

In the following, the principal of the present invention will be described.

In order to resolve the above-described problem and achieve the object, according to a first embodiment of the invention, there is provided a microprobe having a cantilever comprised of a first lever portion having a free end, a second lever portion at a front end portion of which the first lever portion is projected and a support portion for supporting the second lever portion, and a first piezoresistive element for bending the second lever portion provided on the second lever portion.

According to the first embodiment of the invention, by conducting electricity to the first piezoresistive element, an area formed with the first piezoresistive element can be heated and from a difference between thermal expansion coefficients of a surface and a rear face of the second lever portion, at the microprobe per se, the second lever portion can be bent.

Further, according to a second embodiment of the invention, the second lever portion is supported by the support portion in a direction substantially orthogonal to a direction of projecting the first portion, and at least two of the first piezoresistive elements are provided forwardly and rearwardly in the direction of projecting the first lever portion at a portion of the second lever portion connected to the support portion.

According to the second embodiment of the invention, at least two of the first piezoresistive elements are provided at a connecting portion connecting the second lever portion and the support portion and accordingly, by selectively conducting electricity to each of the first piezoresistive elements, a direction of bending the second lever portion can freely be controlled.

Further, according to a third embodiment of the invention, the second lever portion is provided with two of the first lever portions at the front end portion, and two of the first piezoresistive elements are provided on the second lever portion symmetrically with a longitudinal direction of the second lever portion as a central axis.

According to the third embodiment of the invention, two of the first piezoresistive elements are provided symmetrically with the longitudinal direction of the second lever portion as the central axis and accordingly, by selectively conducting electricity to each of the first piezoresistive elements, the second lever portion can be twisted in two directions.

Further, according to a fourth embodiment of the invention, a second piezoresistive element for detecting a bending amount of the first lever portion is provided at a connecting portion for connecting the first lever portion and the second lever portion.

According to the fourth embodiment of the invention, the second piezoresistive element for detecting the bending amount of the first lever portion is provided at the connecting portion for connecting the first lever portion and the second lever portion and accordingly, the second lever portion can be bent and the bending amount of the first lever portion can be detected.

Further, according to a fifth embodiment of the invention, a sharpened stylus is provided on the free end portion of the first lever portion.

According to the fifth embodiment of the invention, the sharpened stylus is provided on the free end portion of the first lever portion and accordingly, bending of the first lever portion transmitted via the stylus can be detected and the stylus can finely be moved by bending the second lever portion.

Further, according to a sixth embodiment of the invention, there is provided a sample surface measuring apparatus characterized in that in a sample surface measuring apparatus for observing a surface of a sample by making a sharpened stylus provided in a microprobe proximate to the surface of the sample and detecting a bending amount of the microprobe by an atomic force caused between the stylus and the surface of the sample, the microprobe according to the fifth embodiment of the invention is used as the microprobe, and the sample surface measuring apparatus comprises driving means for driving the first piezoresistive element provided at the microprobe.

According to the sixth embodiment of the invention, by using the microprobe according to the fifth embodiment, observation on the surface of a sample as in an atomic force microscope can be carried out without providing a fine movement mechanism for making the sample proximate to the stylus of the microprobe.

A detailed explanation will be given of embodiments of a microprobe and a sample surface measuring apparatus according to the invention as follows. Further, the invention is not limited by the embodiments.

(Embodiment) 1

Figure 1:
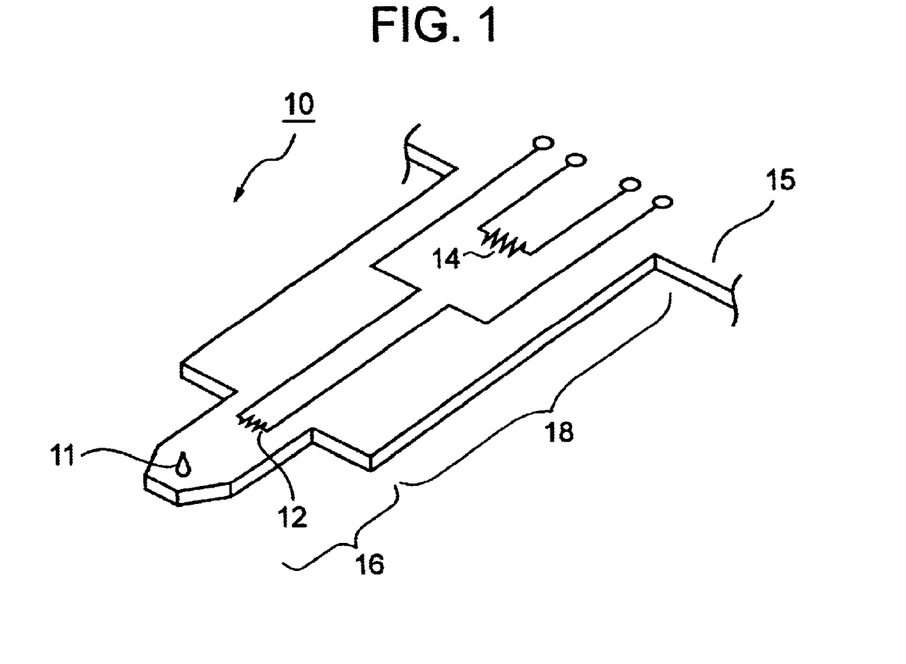
FIG. 1 is a perspective view showing a microprobe according to Embodiment 1.

First, an explanation will be given of a microprobe according to Embodiment 1. FIG. 1 is a perspective view showing a microprobe according to Embodiment 1. As shown in FIG. 1, a microprobe 10 according to Embodiment 1 is constituted by a second lever portion 18 fixed to a support portion 15 and finely moved by an actuator portion, mentioned later, and a first lever portion 16 projected from a front end of the second lever portion 18 and enabling flexible bending by a free end.

Further, in FIG. 1, the above-described first lever portion 16 is provided with a sharpened stylus 11 at its front end portion and is formed with a piezoresistive element 12 functioning as a bending detecting portion at a vicinity of a portion thereof connected to the second lever portion. Meanwhile, the above-described second lever portion 18 is formed with a piezoresistive element 14 functioning as an actuator portion at a vicinity of a portion thereof connected to the support portion 15, further, a conductive layer connected to the piezoresistive element 12 is wired from the first lever portion 16 toward the support portion 15.

Further, in the drawing, a hole portion 28 is provided to exclude weight and volume constituting a hindrance of actuator operation of the piezoresistive element 14 as much as possible such that the operation can effectively be transmitted to the second lever portion 18.

Figure 2:
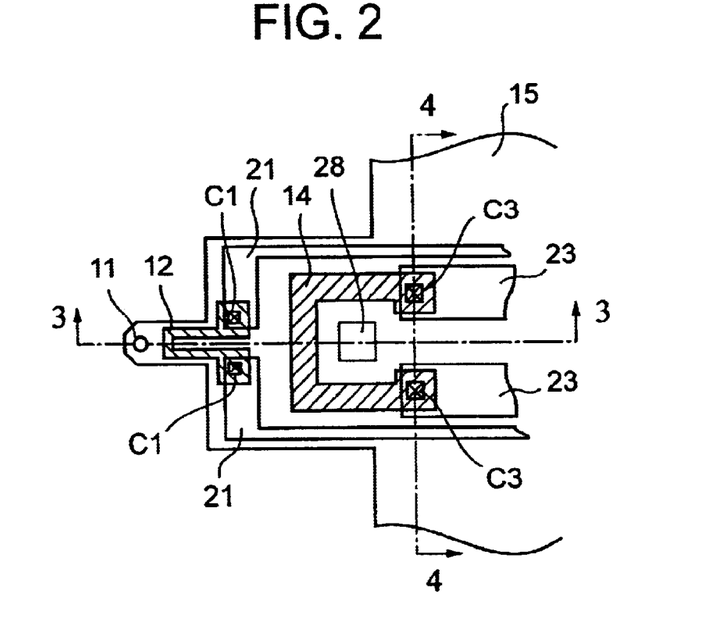
FIG. 2 is a top view of the microprobe according to Embodiment 1.
Figure 3:
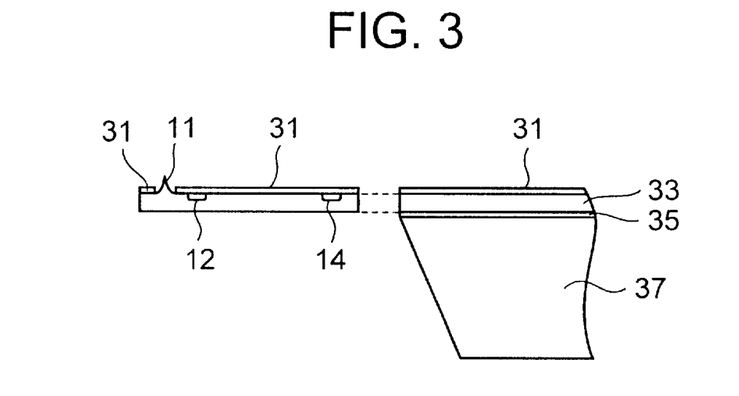
FIG. 3 is a sectional view taken along a line 3—3 of FIG. 2 of the microprobe according to Embodiment 1.
Figure 4:
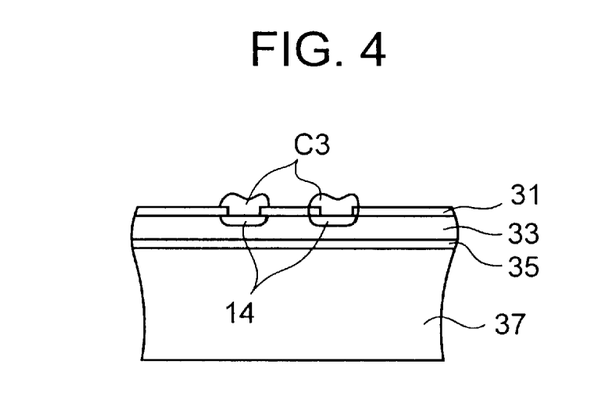
FIG. 4 is a sectional view taken along a line 4—4 of FIG. 2 of the microprobe according to Embodiment 1.

FIG. 2 is a top view of the microprobe according to Embodiment 1, particularly showing wiring structures of the piezoresistive elements 12 and 14. Further, FIG. 3 is a sectional view taken along a line 3—3 of FIG. 2 and FIG. 4 is a sectional view taken along a line 4—4 of FIG. 2. As shown by FIG. 2, at the vicinity of the connecting portion for connecting the first lever portion 16 and and the second lever portion 18, the piezoresistive element 12 is formed in a U-like shape with a line passing through the stylus 11 in the longitudinal direction of the microprobe 10 as a central axis.

Further, at the vicinity of the connecting portion for connecting the second lever portion 18 and the support portion 15, similar to the piezoresistive element 12, the piezoresistive element 14 is formed in a U-like shape with the line passing through the stylus 11 in the longitudinal direction of the microprobe 10 as a central axis.

Further, an insulating layer 31 is formed above the first lever portion 16 excluding the stylus 11, the second lever portion 18 and the support portion 15 and on the piezoresistive elements 12 and 14. Further, in FIG. 2, the insulating layer is not illustrated to facilitate understanding by simplifying the drawing.

On the insulating layer 31, conductive layers 21 constituting wirings of the piezoresistive element 12 are formed from a portion thereof disposed at end portions of the piezoresistive element 12 and the second lever portion 18 to above the support portion 15 via above the second lever portion 18 and conductive layers 23 constituting wirings of the piezoresistive element 14 are formed from end portions of the piezoresistive element 14 to above the support portion 15.

Further, ends of the conductive layers 21 on one side disposed at the second lever portion 18 and the piezoresistive element 12 at a lower layer are electrically connected at metal contact portions C1. Similarly, ends of the conductive layers 23 on one side disposed at the second lever portion 18 and the piezoresistive element 14 at a lower layer are electrically connected at metal contact portions C3.

Further, as shown by FIG. 3 and FIG. 4, the microprobe 10 is fabricated by using a base member formed by SOI (Silicon on Insulator) technology in which an embedded oxide layer ($SiO_2$) 35 is formed on a semiconductor substrate 37 comprising silicon and a silicon layer 33 is thermally pasted together thereabove.

Specifically, the piezoresistive elements 12 and 14 are formed by forming windows in the above-described U-like shape on the silicon layer 33 by a photolithography step and an etching step and implanting impurity ions to the window portion. Generally, carriers having a polarity inverse to the polarity of the silicon layer 33 are implanted. The piezoresistive elements 12 and 14 can be fabricated simultaneously in the same steps. Further, element separation of a high insulation degree is achieved between the piezoresistive elements 12 and 14 by SOI, mentioned above.

Further, the insulating layer 31 and the conductive layers 21 and 23 are respectively formed successively by CVD (chemical Vapor Deposition) or the like. At this occasion, as described above, the piezoresistive element 12 and 14 are electrically connected to the conductive layers 21 and 23 at the metal contact portions C1 and C3.

Next, an explanation will be given of functions of the piezoresistive elements 12 and 14. First, the piezoresistive element 12 functions for detecting a bending amount of the first lever portion 16 and the bending amount is provided as a change in a resistance value of the piezoresistive element 12 which is changed by bending the first lever portion 16. That is, the change in the resistance value can be read from two end portions of the conductive layers 21 disposed above the support potion 15 via the piezoresistive element 12, the metal contact portions C1 and the conductive layers 21.

Meanwhile, the piezoresistive element 14 functions as an actuator portion for displacing the second lever portion 18 in a direction orthogonal to a surface thereof. The displacement is achieved by thermally expanding a peripheral portion of the piezoresistive element 14 by elevating temperature of the piezoresistive element 14 by flowing current to two end portions of the conductive layers 23 disposed above the support portion 15 via the piezoresistive element 14, the metal contact portions C3 and the conductive layers 23.

That is, by using the piezoresistive element 14 as a heater and thermally expanding a surface (face formed with the stylus 11) portion provided with the piezoresistive element 14, the surface portion is elongated relative to a rear face portion thereof, which signifies that the second lever portion 18 is warped in the rear face direction as a result.

Therefore, in a state in which the stylus 11 is made proximate to the surface of the sample, by conducting electricity to the piezoresistive element 14, the stylus 11 can be separated from the surface of the sample. Therefore, with respect to a direction of bending the second lever portion 18, when a direction toward the stylus 11 of the microprobe 10 is defined as minus direction and a direction opposed thereto is defined as plus direction, fine movement only in one direction of the plus direction of Z-axis can be realized, however, by a difference between thermal expansion coefficients of the surface portion and the rear face portion of the second lever portion, fine movement in the minus direction can be carried out.

Figure 5:
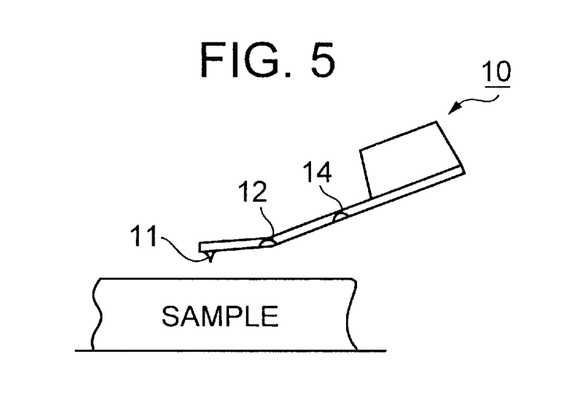
FIG. 5 is a view for explaining an example of use when the microprobe according to Embodiment 1 is used in an atomic force microscope.

Further, also in the case of the piezoresistive element 12 which functions as the bending detecting portion, it is necessary to conduct electricity thereto for reading a change in a resistance value thereof and accordingly, depending on an amount of conducting electricity, the piezoresistive element 12 can function as a heater to thereby bring the first lever portion 16 into a bent state. For example, as shown by FIG. 5, this signifies that observation can be carried out while maintaining a state in which the surface of the first lever portion 16 and the surface of the sample are in parallel with each other.

Thereby, not only mutual action between the stylus 11 and the surface of the sample can be detected with a higher sensitivity but also a space occupied by the microprobe 10 can be reduced. Further, naturally, also the piezoresistive element 14 can realize to maintain the parallel state of the first lever portion 16, mentioned above.

As has been explained above, the microprobe 10 according to Embodiment 1 is constituted by forming the piezoresistive element 14 as the actuator portion for bending the second lever portion 18 in addition to the piezoresistive element 12 functioning as the bending detecting portion on the same surface of the cantilever comprising the first lever portion 16 and the second lever portion 18 and accordingly, fine movement of the microprobe 10 per se in one direction of Z-axis can be realized with low power consumption and at high response speed, further, the piezoresistive element 14 can easily be fabricated along with the piezoresistive element 12 constituting the bending detecting portion by the same steps and accordingly, the microprobe 10 can be provided with a thinner thickness and at lower cost than the conventional microprobe having the Z-axis fine movement function.

(Embodiment) 2

Figure 6:
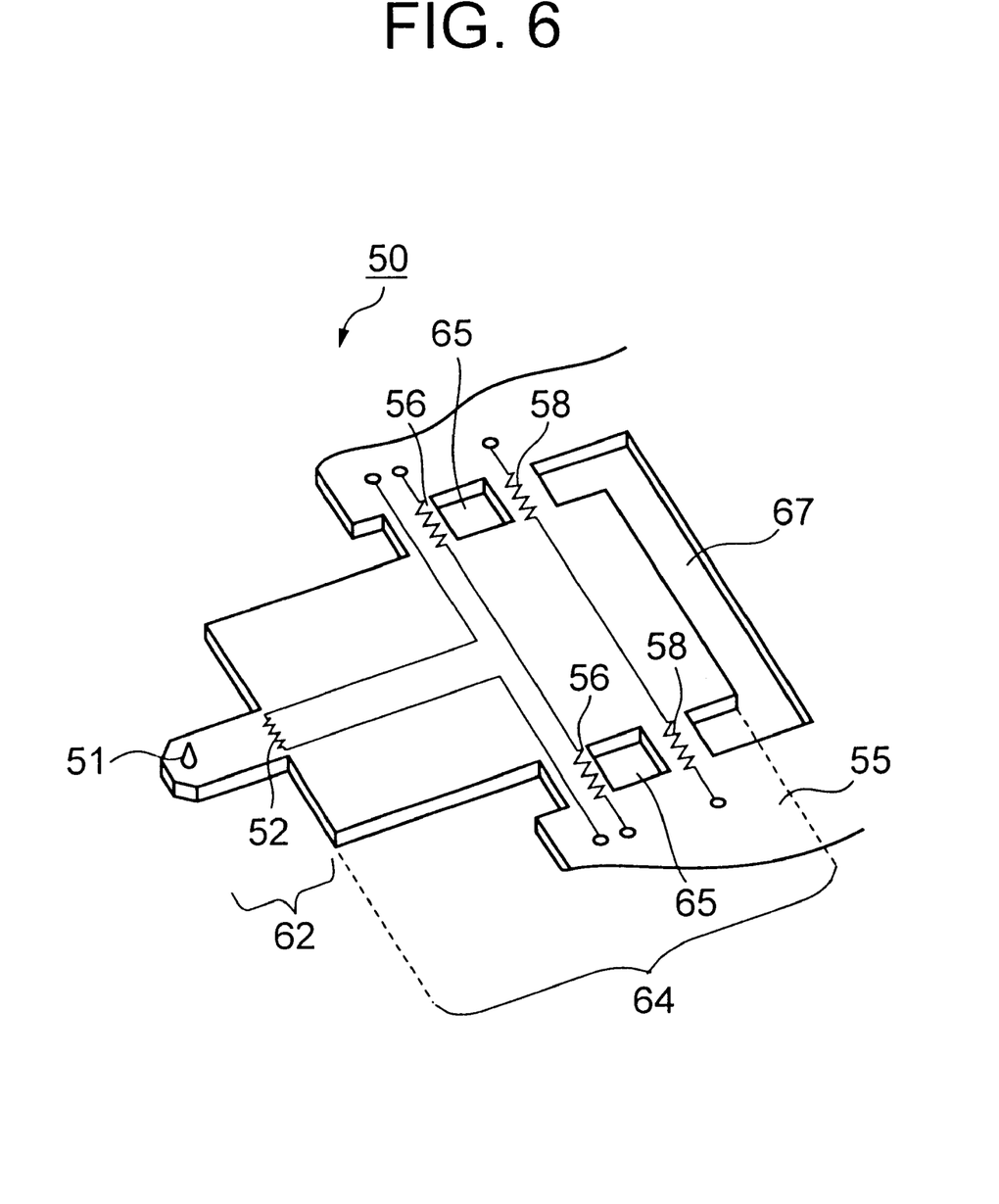
FIG. 6 is a perspective view showing a microprobe according to Embodiment 2.

Next, an explanation will be given of a microprobe according to Embodiment 2. FIG. 6 is a perspective view showing a microprobe according to Embodiment 2. As shown by FIG. 6, a microprobe 50 according to Embodiment 2 is constituted by a second lever portion 64 fixed to a support portion 55 and finely moved by an actuator portion and a first lever portion 62 projected from a front end of the second lever portion 64 and enabling flexible bending by a free end thereof.

Further, in FIG. 6, the above-described first lever portion 62 is provided with a sharpened stylus 51 at its front end portion and formed with a piezoelectric element 52 functioning as a bending detecting portion at a vicinity of a portion thereof connected to the second lever portion. Meanwhile, the above-described second lever portion 64 is formed with piezoresistive elements 56 functioning as a first actuator portion and piezoresistive elements 58 functioning as a second actuator portion at a vicinity of a portion thereof connected to the support portion 55, further, a conductive layer connected to the piezoresistive element 52 is wired from the first lever portion 62 toward the support portion 55.

Further, in the drawing, hole portions 65 and 67 are provided to exclude weight and volume constituting a hindrance of actuator operation of the piezoresistive elements 56 and 58 as much as possible such that operation can effectively be transmitted to the second lever portion 64. Further, steps of forming the piezoresistive elements 52, 56 and 58 shown in FIG. 6 are similar to the steps of forming the piezoresistive elements explained in Embodiment 1 and accordingly, an explanation thereof will be omitted here.

As shown by FIG. 6, the microprobe 50 is formed with two sets of the piezoresistive elements 56 and 58 forwardly and rearwardly in the longitudinal direction above the second lever portion 64 and accordingly, by conducting electricity selectively to either ones of the piezoresistive elements 56 and 58, the fine movement can be controlled in plus direction as well as minus direction in the Z-axis direction by a thermally expanded state of the second lever portion 64.

Further, the piezoresistive element 52 in the drawing operates similar to the piezoresistive element 12 explained in Embodiment 1, further, according to the microprobe 50, as shown by FIG. 5, by adjusting an amount of conducting electricity to the piezoresistive element 52 or the piezoresistive elements 56 and 58, a state in which a surface of the first lever portion 62 and the surface of the sample are in parallel with each other can be maintained.

As has been explained, the microprobe 50 according to Embodiment 2 is constituted by forming the piezoresistive elements 56 and 58 as the actuator portion for bending the second lever portion 64 in addition to the piezoresistive element 52 functioning as the bending detecting portion on the same surface of the cantilever comprising the first lever portion 62 and the second lever portion 64 and accordingly, the fine movement of the microprobe 50 per se in two directions of the Z-axis can be realized with low power consumption and at high response speed, further, the piezoresistive elements 56 and 58 can easily be fabricated along with the piezoresistive element 52 constituting the bending detecting portion by the same steps and accordingly, the microprobe 50 can be provided with thinner thickness and at lower price than the conventional microprobe having the Z-axis fine movement function.

(Embodiment) 3

Figure 7:
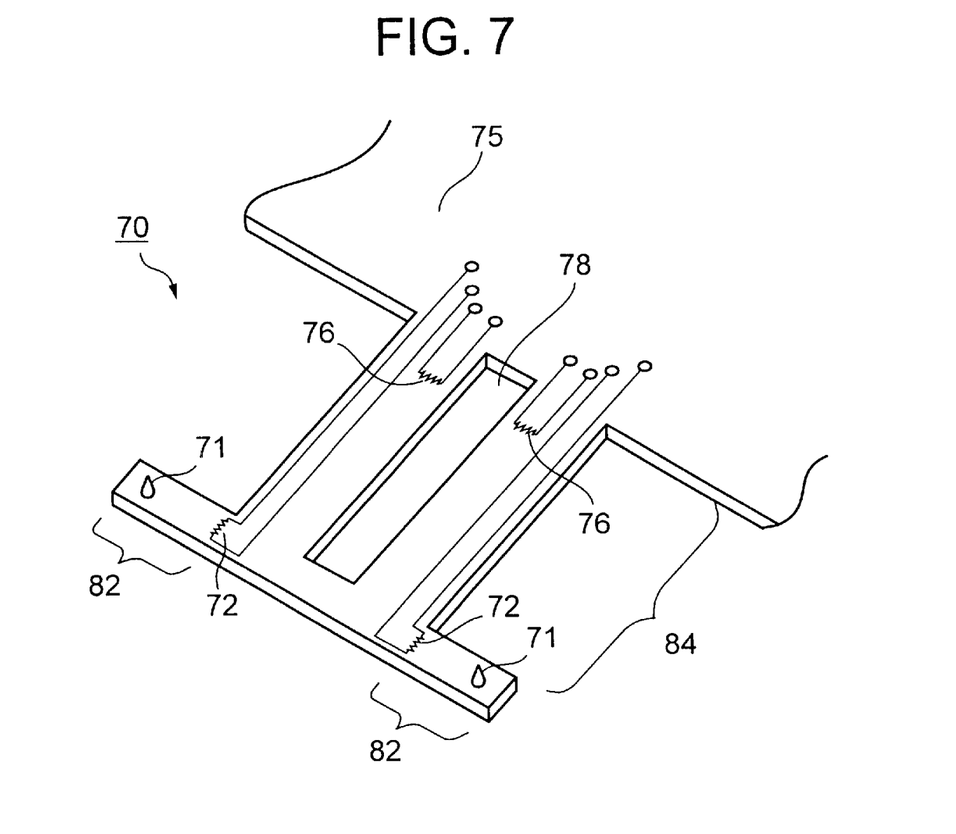
FIG. 7 is a perspective view showing a microprobe according to Embodiment 3.

Next, an explanation will be given of a microprobe according to Embodiment 3. FIG. 7 is a perspective view showing a microprobe according to Embodiment 3. As shown by FIG. 7, a microprobe 70 according to Embodiment 3 is constituted by a second lever portion 84 fixed to a support portion 75 and finely moved by an actuator portion and two of first lever portions 82 projected from a front end of the second lever portion 84 in two side directions and enabling flexible bending by free ends thereof.

Further, in FIG. 7, the above-described two first lever portions 82 are provided with sharpened styluses 71 at respective front end portions thereof and formed with piezoresistive elements 72 functioning as bending detecting portions at vicinities of portions thereof connected to the second lever portion 84. Meanwhile, the above-described second lever portion 84 is formed with two of piezoresistive elements 76 functioning as actuator portions at vicinities of portions thereof connected to the support portion 75, further, a conductive layer connected to the piezoresistive elements 72 is wired from the first lever portion 82 toward the support portion 75.

Further, in the drawing, a hole portion 78 is provided to exclude weight and volume constituting a hinderance of actuator operation of two of the piezoresistive elements 76 as much as possible such that the operation can effectively be transmitted to the second lever portion 84. Further, steps of forming the piezoresistive elements 72 and 76 shown in FIG. 7 are similar to the steps of forming the piezoresistive elements explained in Embodiment 1 and accordingly, an explanation thereof will be omitted here.

As shown in FIG. 7, the microprobe 70 is formed with two sets of the piezoresistive elements 72 and 76 symmetrically with the hole portion 78 formed in the longitudinal direction of the second lever portion 84 as a central axis. In this case, the respective piezoresistive elements 72 are provided with a function the same as that of the piezoresistive element 12 explained in Embodiment 1 for detecting bending amounts of the first lever portions 82. Further, the respective piezoresistive elements 76 are provided with a function the same as that of the piezoresistive element 14 explained in Embodiment 1 for finely moving the second lever portion 14 in Z-axis direction.

Figure 8:
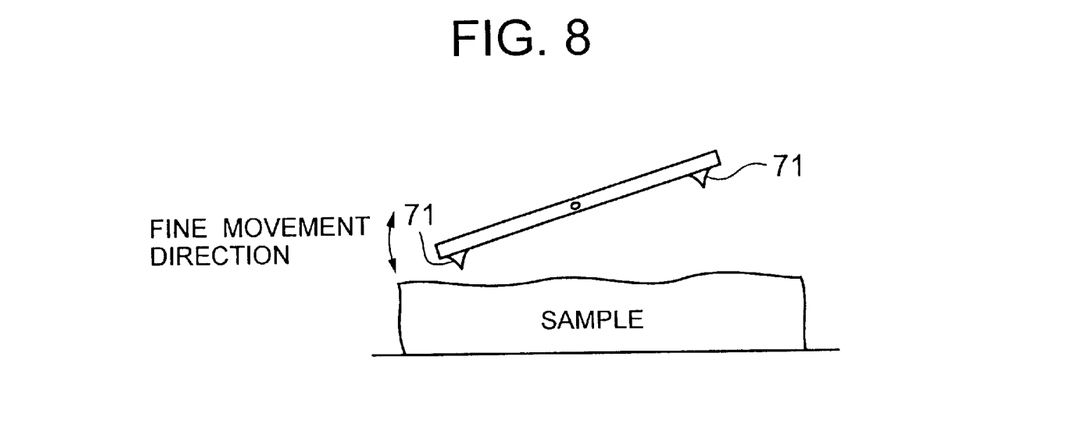
FIG. 8 is a view for explaining an example of use when the microprobe according to Embodiment 3 is used in an atomic force microscope.

In this way, by providing sets comprising the piezoresistive elements 72 functioning as the bending detecting portions and the piezoresistive elements 76 functioning as the actuator portions symmetrically on the left and on the right, by operating the piezoresistive element 76 belonging to either one set of the two sets, there is formed a twisted state as shown in FIG. 8, thereby, when attention is paid to one of the styluses 71, the stylus 11 can finely be moved in plus direction and minus direction of Z-axis relative to the surface of the sample.

As has been explained above, the microprobe 70 according to Embodiment 3 is constituted by forming the sets comprising the piezoresistive elements 72 functioning as the bending detecting portions and the piezoresistive elements 76 functioning as the actuator portions for bending the second lever portion 84 symmetrically in the longitudinal direction of the second lever portion 84 on the same surface of the cantilever comprising the first lever portion 82 and the second lever portion 84 and accordingly, for example, when the sample is observed by using the stylus 71 belonging to one of the sets, by conducting electricity to the piezoresistive element 76 belonging to the same set, the stylus 71 can be separated from the surface of the sample and by conducting electricity to the piezoelectric element 76 belonging to other set, the above-described stylus 71 can be proximate to the surface of the sample, that is, fine movement of the microprobe 70 per se in two directions of the Z-axis can be realized with low power consumption and at high response speed, further, the respective piezoelectric elements 76 can easily be fabricated along with the piezoresistive elements 72 constituting the bending detecting portions by the same steps and accordingly, the microprobe 70 can be provided with a thinner thickness and at lower cost than the conventional microprobe having the Z-axis fine movement function.

(Embodiment) 4

Figure 9:
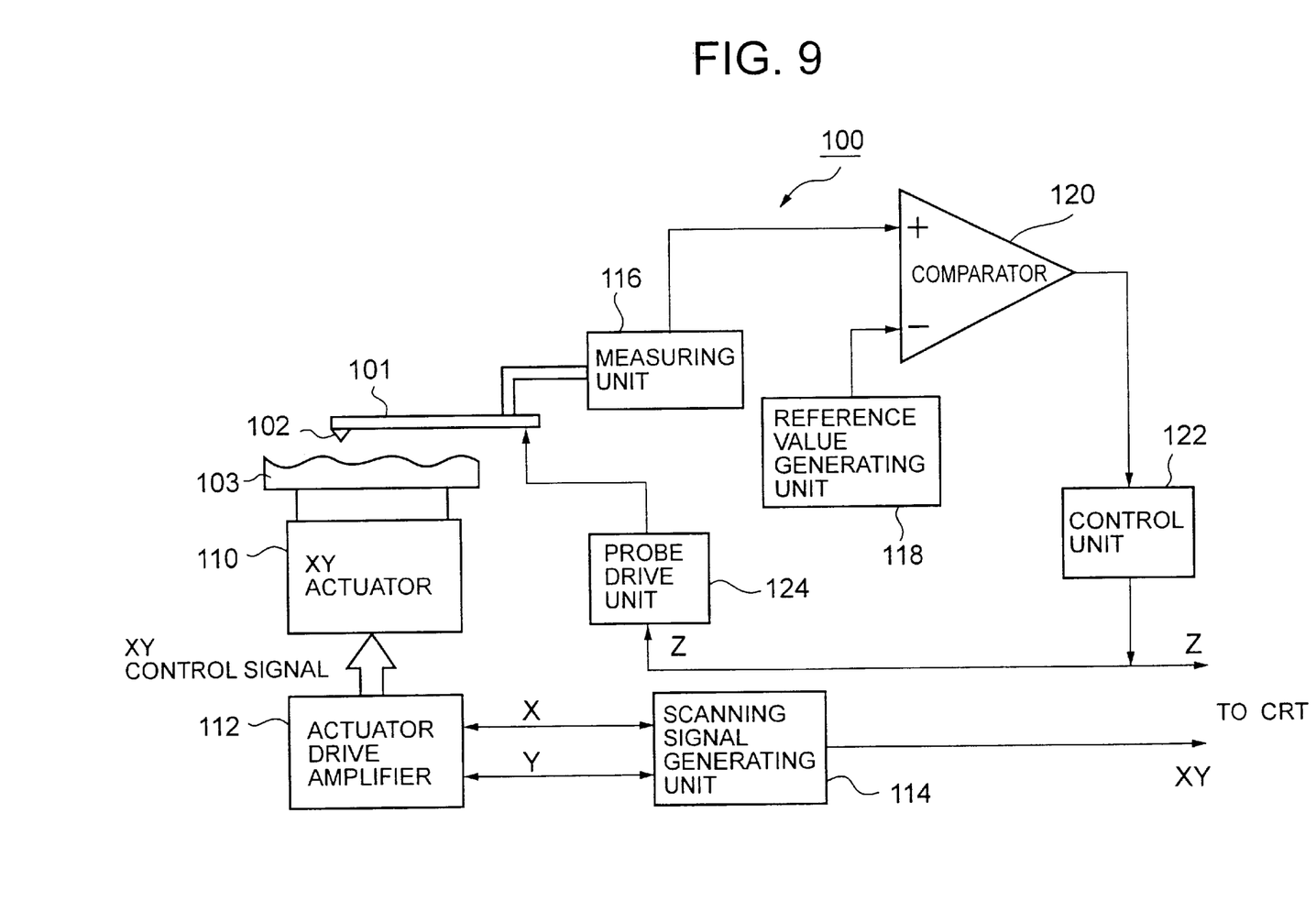
FIG. 9 is a block diagram showing an outline constitution of a sample surface measuring apparatus according to Embodiment 4.

Next, an explanation will be given of a sample surface measuring apparatus according to Embodiment 4. FIG. 9 is a block diagram showing an outline constitution of an atomic force microscope using the microprobes described in Embodiments 1 through 3, mentioned above. In FIG. 9, a sample surface measuring apparatus 100 comprises a microprobe 101 (corresponding to the above-described microprobe 10, 50, 70) provided with a sharpened stylus 102 at a front end portion thereof directed to a surface of a sample 103, an XY actuator 110 for finely moving the sample 103 in the horizontal direction (X, Y directions) relative to the microprobe 101, an actuator drive amplifier 112 for generating an XY control signal for driving the XY actuator 110, a scanning signal generating unit 114 for generating a signal (scanning signal) for finely moving the sample 103 at constant speed in a predetermined range in X and Y directions, mentioned above, a measuring unit 116 for acquiring a detection signal provided from a bending detecting portion (the above-described detector: piezoresistive element) on the microprobe 101, a reference value generating unit 118 for generating a detection value in a steady state of the above-described bending detecting portion, that is, a reference value for detecting irregularities of the surface of the sample 103, a comparator 120 for deriving an actual bending amount of the microprobe 101 by comparing signals provided respectively from the measuring unit 116 and the reference value generating unit 118, a control unit 122 for generating a signal in correspondence with a displacement in Z-direction of the XY actuator 110 based on a signal provided from the comparator 120 and a probe drive unit 124 for driving an actuator portion provided on the microprobe 101.

A brief explanation will be given of operation of the atomic force microscope 100 as follows. Further, first, a user fixes the sample 103 constituting an observation object onto a stage on the XY actuator 110 and attaches the microprobe 101 at a comparatively remote position thereabove.

After preparation for carrying out observation of the sample has been finished, successively, it is necessary to make the microprobe 101 proximate to the sample 103 sufficiently to a degree by which the stylus 202 causes atomic force between the stylus 202 and the surface of the sample 203. The proximity control is carried out by a Z-axis rough movement mechanism (not illustrated) and is finished when the measuring unit 116 can acquire a predetermined amount of signal from the above-described bending detecting portion.

Further, the above-described predetermined amount of signal acquired at the measuring unit 116 is a signal indicating detection of atomic force between the stylus 102 and the surface of the sample 103 and is actually informed by a signal outputted from the comparator 120. In this case, a resistance value of the piezoresistive element per se constituting the bending detecting portion is varied by conditions other than bending such as temperature condition or the like and accordingly, the reference value of the reference value generating unit 118 constituting one of comparison objects of the comparator 120 provides a reference resistance value for removing the unnecessary variation information from a variation in the resistance value measured at the bending detecting portion.

After finishing the above-described proximity control, at the scanning signal generating unit 114, there is generated a scanning signal for instructing movement in a predetermined range set on a computer (not illustrated), that is, a plane range (XY range) in the XY actuator 110. The scanning signal is normally a signal for realizing raster scanning.

Further, the scanning signal is inputted to the actuator drive amplifier 112, amplified pertinently to current or voltage sufficient for driving the XY actuator 110 and thereafter inputted to the XY actuator 110 as an XY control signal. The XY actuator 110 actually moves the sample 103 on the stage in X and Y directions by an input of the XY control signal.

While the movement on an XY plane of the sample 103 is being repeated by the above-described XY actuator 110, the measuring unit 116 acquires a signal always from the bending detecting portion of the microprobe 101 and a signal in correspondence with an amount of bending the microprobe 101 is outputted from the comparator 120.

In this case, the bending constant mode, mentioned above, in measurement modes of the sample surface measuring apparatus 100 is realized by controlling the actuator portion on the microprobe 101 by a feedback control via the probe drive portion 124 such that the amount of bending the microprobe 101 stays constant and regarding a control signal required for the feedback control as an irregularity signal of the sample 103.

Therefore, the sample 103 is moved in a constant range on the XY plane and is finely moved in Z-axis direction by the feedback control of the actuator portion of the microprobe 101 under the bending constant mode. Simultaneously therewith, the XY control signal accompanied by operation of the above-described XY actuator 110 and the Z control signal are inputted to a display apparatus (CRT), thereby, a user can be informed of surface information of the sample 103.

As has been explained above, the sample surface measuring apparatus 100 according to Embodiment 4 can carry out sample surface measurement similar to that in the conventional apparatus without including the Z-axis fine movement mechanism which has conventionally been necessary for finely moving the sample 103 in the Z-axis direction by using the microprobe 10, 50 or 70 shown in Embodiments 1 through 3 and accordingly, the constitution of the apparatus can be prevented from being complicated and expensive and power necessary for using thereof can be reduced.

Further, although according to the above-described embodiments 1 through 3, there has been pointed out as examples, the microprobes each can be used for the atomic force microscope by providing the stylus at the front end of the first lever portion and providing the piezoresistive element functioning as the bending detecting portion at the connecting portion for connecting the first lever portion and the second lever portion, sufficient value is provided to a microprobe provided with only a piezoresistive element functioning as an actuator portion for bending the second lever portion without providing the stylus or the piezoresistive element functioning as the bending detecting portion. For example, such a microprobe becomes useful when conduction test is carried out to a plurality of electrodes at narrow intervals arranged in an integrated circuit or the like, in the case of physically making ON/OFF electric connection with an outside test apparatus.

According to the invention described above, since the first piezoresistive element is formed on the second lever portion, by conducting electricity thereto, an area formed with the first piezoresistive element can be heated, from a difference between thermal expansion coefficients of a surface and a rear face of the second lever portion, in the microprobe per se, the second lever portion can be bent and accordingly, there is achieved an effect in which in comparison with an example of using a conventional piezoelectric element, a microprobe having a self finely movement function can be provided by a constitution having a thin thickness, with low power consumption, at high response speed and at low cost.

Further, according to the invention described above, at least two of the first piezoresistive elements are provided at the connecting portion for connecting the second lever portion and the support portion and accordingly, by selectively conducting electricity to each of the first piezoresistive elements, the direction of bending the second lever portion can freely be controlled and accordingly, there is achieved an effect in which in comparison with an example of using a conventional piezoelectric element, a microprobe having self finely movement function can be provided by a constitution having a thin thickness, with low power consumption, at high response speed and at low cost.

Further, according to the invention described above, two of the first piezoresistive elements are provided symmetrically with the longitudinal direction of the second lever portion as the central axis on the second lever portion and accordingly, by selectively conducting electricity to each of the first piezoresistive elements, the second lever portion can be twisted in two directions and therefore, there is achieved an effect in which in comparison with an example of using a conventional piezoelectric element, a microprobe having self finely movement function can be provided by a constitution having a thin thickness, with low power consumption, at high response speed and at low cost.

Further, according to the invention described above, the second piezoresistive element for detecting the bending amount of the first lever portion is provided at the connecting portion for connecting the first lever portion and the second lever portion and accordingly, the second lever portion can be bent and the bending amount of the first lever portion can be detected and accordingly, there is achieved an effect in which in comparison with an example of using a conventional piezoelectric element, a microprobe having self finely movement function can be provided by a constitution having a thin thickness, with low power consumption, at high response speed and at low cost and the second piezoresistive element can easily be fabricated by steps the same as those of the first piezoresistive element.

Further, according to the invention described above, the sharpened stylus is provided on the free end portion of the first lever portion and accordingly, there is achieved an effect in which bending of the first lever portion transmitted via the stylus can be detected, the stylus can finely be moved by bending the second lever portion and the microprobe can be used as a microprobe for the atomic force microscope.

Further, according to the invention described above, there is achieved an effect in which observation of the surface of the sample as in the atomic force microscope can be carried out without providing a fine movement mechanism for making the sample proximate to the stylus of the microprobe.

What is claimed is:

1. A microprobe comprising: a cantilever having at least one first lever portion having a free end portion, a second lever portion having a first end from which the first lever portion projects and a second end opposite to the first end, and a support portion connected to the second end of the second lever portion for supporting the second lever portion; and at least one first piezoresistive element disposed on the second lever portion for bending the second lever portion to displace the first lever portion.

2. A microprobe according to claim 1; wherein the second lever portion is supported by the support portion in a direction substantially orthogonal to a direction in which the first lever portion projects from the second lever portion; and wherein the at least one piezoresistive element comprises at least two first piezoresistive elements extending in the direction of projection of the first lever portion and disposed at a portion of the second end of the second lever portion connected to the support portion.

3. A microprobe according to claim 1; wherein the at least one first lever portion comprises two first lever portions extending from the first end of the second lever portion; and wherein the at least one piezoresistive element comprises two first piezoresistive elements disposed on the second lever portion symmetrically to a central longitudinal axis of the second lever portion.

4. A microprobe according to claim 3; further comprising a second piezoresistive element disposed at a connecting portion between the first lever portion and the second lever portion for detecting a bending amount of the first lever portion.

5. A microprobe according to claim 4; further comprising a sharpened stylus disposed on the free end portion of the first lever portion.

6. A sample surface measuring apparatus for observing a surface of a sample, the sample surface measuring apparatus comprising: a microprobe comprised of a cantilever having at least one first lever portion having a free end portion, a second lever portion having a first end from which the first lever portion projects and a second end opposite to the first end, a support portion connected to the second end of the second lever portion for supporting the second lever portion, and at least one first piezoresistive element disposed on the second lever portion for bending the second lever portion to displace the first lever portion; and driving means for driving the first piezoresistive element of the microprobe.

7. A microprobe according to claim 1; further comprising a second piezoresistive element disposed at a connecting portion between the first lever portion and the second lever portion for detecting a bending amount of the first lever portion.

8. A microprobe according to claim 1; further comprising a sharpened stylus disposed on the free end portion of the first lever portion.

9. A microprobe according to claim 2; further comprising a second piezoresistive element disposed at a connecting portion between the first lever portion and the second lever portion for detecting a bending amount of the first lever portion.

10. A microprobe according to claim 2; further comprising a sharpened stylus disposed on the free end portion of the first lever portion.

11. A microprobe according to claim 3; further comprising a sharpened stylus disposed on the free end portion of the first lever portion.

12. A sample surface measuring apparatus according to claim 6; wherein the second lever portion is supported by the support portion in a direction substantially orthogonal to a direction in which the first lever portion projects from the second lever portion; and wherein the at least one piezoresistive element comprises at least two first piezoresistive elements extending in the direction of projection of the first lever portion and disposed at a portion at the second end of the second lever portion connected to the support portion.

13. A sample surface measuring apparatus according to claim 6; wherein the at least one first lever portion comprises two first lever portions extending from the first end of the second lever portion; and wherein the at least one piezoresistive element comprises two first piezoresistive elements disposed on the second lever portion symmetrically to a central longitudinal axis of the second lever portion.

14. A sample surface measuring apparatus according to claim 6; further comprising a second piezoresistive element disposed at a connecting portion between the first lever portion and the second lever portion for detecting a bending amount of the first lever portion.

15. A sample surface measuring apparatus according to claim 6; further comprising a sharpened stylus disposed on the free end portion of the first lever portion.

16. A sample surface measuring apparatus according to claim 15; further comprising moving means for effecting movement between the microprobe and a surface of a sample to bring the sharpened stylus provided proximate to the surface of the sample for detecting a bending amount of the microprobe by an atomic force caused between the sharpened stylus and the surface of the sample.

17. A microprobe comprising: a cantilever having a first lever portion, a second lever portion connected to the first lever portion at a first connection portion, and a support portion connected to the second lever portion at a second connection portion for supporting the second lever portion; a first piezoresistive element disposed proximate the second connection portion for displacing the second lever portion along with the first lever portion; and a second piezoresistive element disposed proximate the first connection portion for detecting a displacement amount of the first lever portion.

18. A microprobe according to claim 17; further comprising a sharpened stylus extending from a free end portion of the first lever portion.

19. A sample surface measuring apparatus for observing a surface of a sample, the sample surface measuring apparatus comprising: a microprobe according to claim 17; and driving means for driving the first piezoresistive element of the microprobe.

20. A sample surface measuring apparatus according to claim 19; further comprising a sharpened stylus disposed on the free end portion of the first lever portion of the microprobe.

* * * * *